United States Patent [19]

Furusaki et al.

[11] Patent Number: 5,189,225
[45] Date of Patent: Feb. 23, 1993

[54] PROCESS FOR CATALYTICALLY PRODUCING MONOALKYLETHER OF DIHYDRIC PHENOL COMPOUND

[75] Inventors: Shinichi Furusaki; Masaoki Matsuda; Muneki Saito; Yasushi Shiomi; Yasuo Nakamura; Michio Tobita, all of Ube, Japan

[73] Assignee: Ube Industries, Ltd., Yamaguchi, Japan

[21] Appl. No.: 589,612

[22] Filed: Sep. 28, 1990

[30] Foreign Application Priority Data

Sep. 29, 1989 [JP] Japan ................................. 1-251977
Jul. 13, 1990 [JP] Japan ................................. 2-184103

[51] Int. Cl.$^5$ ............................................ C07C 41/01
[52] U.S. Cl. .................................. 568/649; 568/650; 568/652; 568/653
[58] Field of Search ............... 568/648, 649, 650, 652, 568/653

[56] References Cited

U.S. PATENT DOCUMENTS 4,025,566  5/1977  Nagai et al. ......................... 568/652

FOREIGN PATENT DOCUMENTS 827803    1/1952  Fed. Rep. of Germany .
53-35062  9/1978  Japan .
55-6618   2/1980  Japan .
55-33658  9/1980  Japan .
56-25213  6/1981  Japan .

OTHER PUBLICATIONS

Bond, *Heterogeneous Catalysis: Principles and Applications* 2nd Edition, 1987, pp. 70–74.
Freidlin et al., Chemical Abstracts, vol. 55, p. 7336 (1960).
Matsuzaki et al., Journal of Japan Chemical Association, No. 12, pp. 2331–2334 (1985) with English Abstract.
Matsuzaki et al., Chemistry and Industry, pp. 35–36 (Jan. 6, 1986).

*Primary Examiner*—Alan Siegel
*Assistant Examiner*—Margaret J. Page
*Attorney, Agent, or Firm*—Finnegan, Henderson, Farabow, Garrett, Dunner

[57] ABSTRACT

A monoalkylether of dihydric phenol compound is produced by bringing a feed gas comprising a mixture gas of a dihydric phenol compound with a monohydric alcohol compound into contact with an active catalyst component comprising at least one member selected from phosphorus compounds, and mixtures and reaction products of phosphorus compounds with boron compounds and carried on an inert solid carrier consisting of, for example, α-alumina, γ-alumina, activated carbon or titania grains, and preferably having a pore volume of 0.1 ml/g or more and a specific surface area of 1 m$^2$/g or more, at a temperature of 200° C. to 400° C., and collecting the resultant reaction product from the reaction mixture.

12 Claims, 4 Drawing Sheets

PROCESS FOR CATALYTICALLY PRODUCING MONOALKYLETHER OF DIHYDRIC PHENOL COMPOUND

BACKGROUND OF THE INVENTION

1) Field of the Invention

The present invention relates to a process for catalytically producing a monoalkylether of a dihydric phenol compound.

More particularly, the present invention relates to a process for catalytically producing a monoalkylether of a dihydric phenol compound in gas phase in the presence of a specific catalyst component comprising a phosphorus compound, a mixture of a phosphorus compound with a boron compound, or a boron-phosphorus compound, and carried on an inert solid carrier, at a high conversion and at a high yield, in a stable condition for a long time.

The monoalkylethers of dihydric phenol compounds, for example, guaiacol, are useful as intermediates of various perfumes and medicines.

2) Description of the Related Arts

It is known that a monoalkylether of a dihydric phenol compound can be produced by a reaction of a dihydric phenol compound with an etherifying agent, by various methods.

In a known method, a monoalkylether of a dihydric phenol compound is produced by etherifying the dihydric phenol compound with an alkylating agent, for example, dimethyl sulfate, a combination of alkyl chloride with an alkali, or dimethyl carbonate in a liquid phase.

Generally, the alkylating agent usable for the liquid phase etherifying process is extremely expensive, and thus the waste liquid from the etherifying process must be clarified by a complicated process.

Various gas phase etherifying processes for producing the monoalkylethers of the dihydric phenol compounds are disclosed in the following literature:

(1) Chem. Abs., 55-7336 (1960) Masloboino-Zhirovaya Prom., 26 [10], 24 to 27 (1960)
(2) West German Patent No. 827803
(3) Japanese Examined Patent Publication NO. 53-35062
(4) Japanese Examined Patent Publication No. 55-33658
(5) Japanese Examined Patent Publication No. 55-6618
(6) Journal of Japan Chemical Association, [12], 23311(1985)
(7) Japanese Examined Patent Publication No. 56-25213

For example, an etherifying reaction of a dihydric phenol compound, for example, catechol, with a lower monohydric alcohol, for example, methyl alcohol, is carried out in a gas phase in the presence of a catalyst prepared from phosphoric acid and boric acid, as disclosed in literatures (1) and (2), or with another catalyst comprising aluminum, phosphorus, boron and oxygen, as disclosed in literatures (3), (4) and (5), or with still another catalyst consisting of kaolin, as disclosed in literature (6) or (7), to produce a monoalkylether of the dihydric phenol compound, for example guaiacol.

The prior art disclosed in literatures (1) and (2), in which the catalyst comprises phosphoric acid and boric acid, is disadvantageous in that the conversion to the monoalkylether is made at an unsatisfactory level of 80 to 90%, and an active catalytic component produced by the reaction of phosphoric acid with boric acid, i.e., boron phosphate ($BPO_4$), is consumed with a lapse of time, and therefore, the durability of the catalyst is not long enough for industrial use.

The prior art process disclosed in literatures (3), (4) and (5) in which the catalyst comprises aluminum, boron, phosphorus, and oxygen is advantageous in that the conversion to the monoalkylether of the dihydric phenol compound is high and the duration of the $BPO_4$ is improved, but is disadvantageous in that the activity of the catalyst is reduced with a lapse of time during a long time operation, due to the consumption of $BPO_4$ and an adhesion of carbon to the catalyst surface, and the mechanical strength is also gradually lowered with a lapse of time. Therefore, the durability of the catalyst must be further improved. Further, this catalyst is disadvantageous is that, when a lowering of the activity of the catalyst occurs, the reaction temperature must be raised in line with this lowering of the catalyst activity, to maintain the conversion of the dihydric phenolic compound to the monoalkylether thereof at a desired high level, and therefore, it is very difficult to continue the etherifying reaction in a stable condition for a long time.

In the process in which the catalyst consisting of kaolin is used, the conversion to the monoalkylether of the dihydric phenol compound is obtained at an unsatisfactory low level of about 80%, and an undesirable by-product is formed in a large amount of about 10%. Therefore, this process is not practical for industrial use.

SUMMARY OF THE INVENTION

An object of the present invention is to provide a process for catalytically producing a monoalkylether of a dihydric phenol compound in a gas phase by an etherifying reaction of a dihydric phenol compound with a lower monohydric alcohol compound, at a high conversion and at a high selectivity.

Another object of the present invention is to provide a process for catalytically producing a monoalkylether of dihydric phenol compound in a gas phase from a dihydric phenol compound and a lower monohydric alcohol compound, in a stable condition for a long time.

The above-mentioned objects can be attained by the process of the present invention which comprises the steps of bringing a feed gas comprising a mixture of a dihydric phenol compound and a lower monohydric alcohol compound in a gas phase into contact with an active catalyst component comprising at least one member selected from the group consisting of phosphorus compounds, and mixtures and reaction products of phosphorus compounds with boron compounds, and carried on an inert solid carrier in a reactor, at a temperature of 200° C. to 400° C., and collecting the resultant reaction product from the reaction mixture.

In an embodiment of the process of the present invention, the active catalyst component is fed together with the feed gas into the reactor, while allowing the inert solid carrier to be impregnated with the fed active catalyst component.

In another embodiment of the process of the present invention, the inert solid carrier is previously impregnated with the active catalyst component.

DESCRIPTION OF THE PREFERRED EMBODIMENTS

Figure 1:
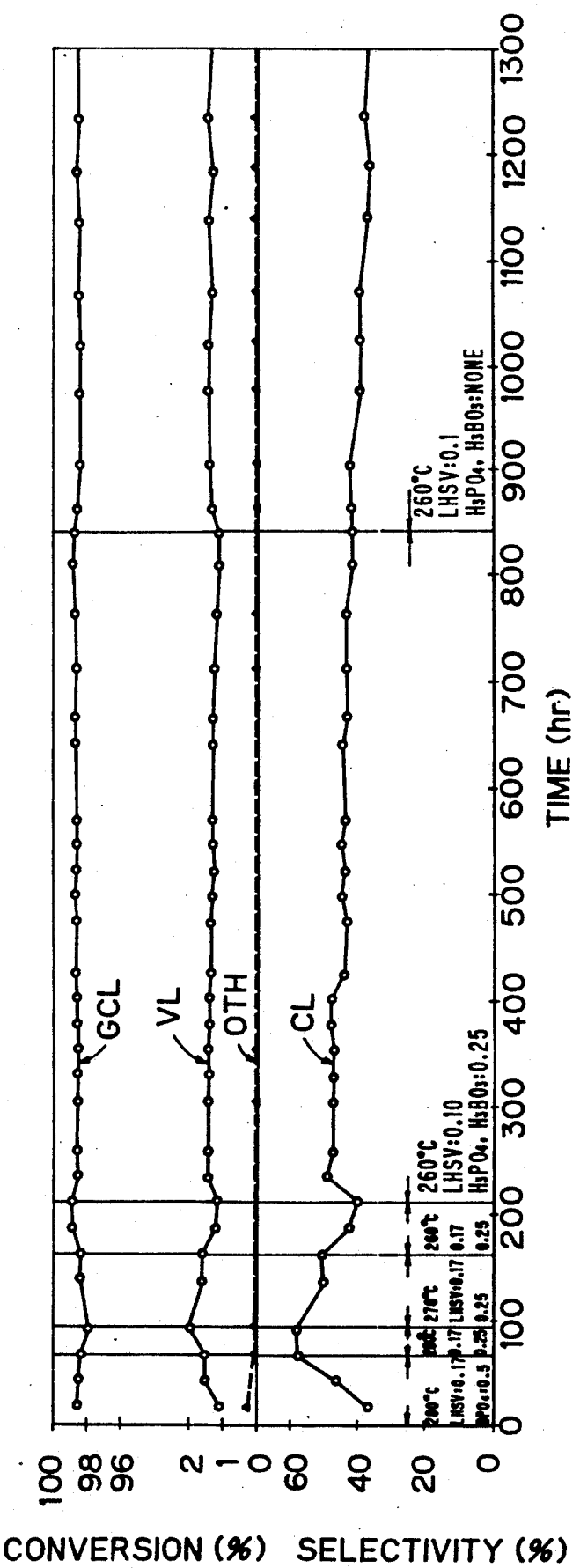
FIG. 1 is a graph showing changes in the conversion of catechol (CL) and selectivities of guaiacol (GCL), veratrol (VL) and other by-products (OTH) with a lapse of the reaction time, when a catechol—methyl alcohol mixture gas containing a catalytic amount of an active catalyst component (phosphoric acid and boric acid) is continuously introduced into a reactor containing an inert solid carrier consisting of α-alumina grains with a pore volume of 0.4 ml/g and a specific surface area of 48.1 m$^2$/g, to cause the active catalyst component to be impregnated in the inert solid carrier and the catechol to be mono-etherified with the methyl alcohol.
Figure 1:
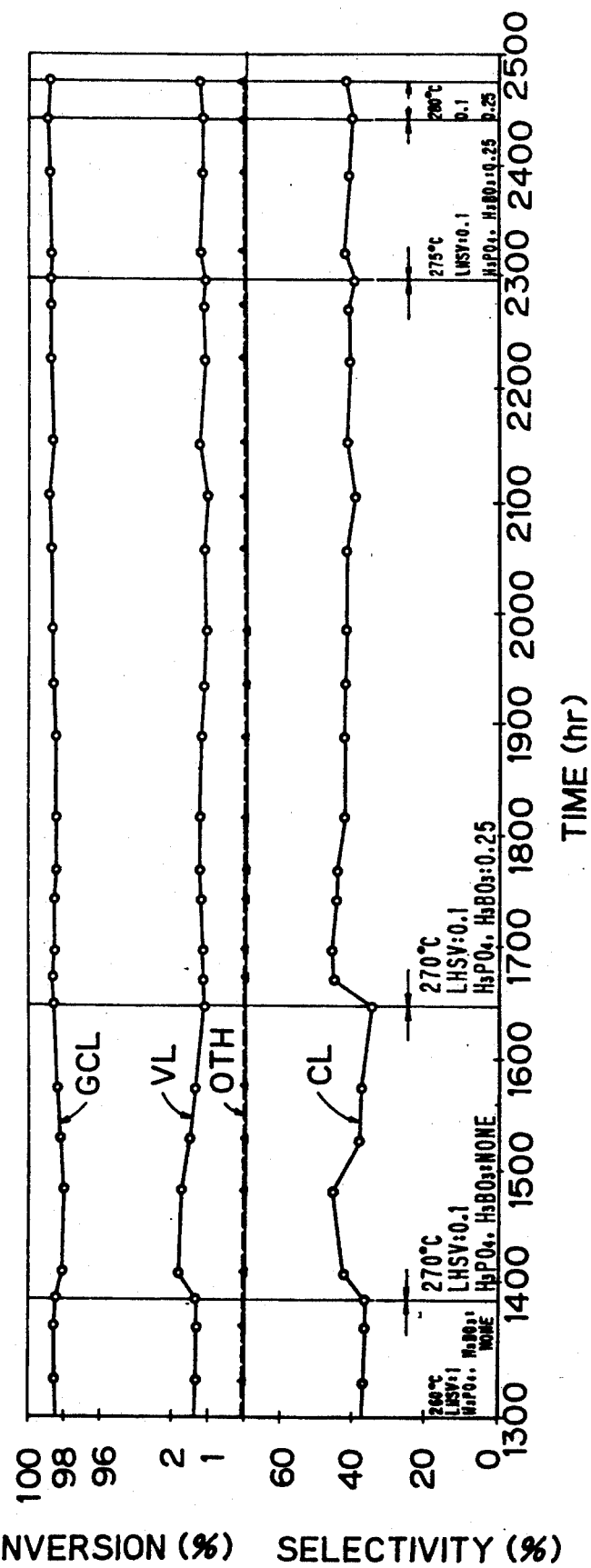

In the process of the present invention, a feed gas comprising a mixture of a dihydric phenol compound and a lower monohydric alcohol compound in a gas phase is brought into contact with an active catalyst component comprising at least one member selected from the group consisting of phosphorus compounds, and mixtures and reaction products of phosphorus compounds with boron compounds, and carried on an inert solid carrier in a reactor, at a temperature of from 200° C. to 400° C.

In an embodiment of the process of the present invention, the feed gas is prepared by vaporizing a mixture of a solution of a dihydric phenol compound in a lower monohydric alcohol compound in a vaporization device. The resultant feed gas (mixture gas) is fed into a reactor (reactor vessel or tube) containing a catalyst consisting of an inert solid carrier composed of a number of inert solid grains previously impregnated with an active catalyst component, and brought into contact with the active catalyst component carried on the inert solid carrier.

In another embodiment of the process of the present invention, the dihydric phenol compound and the monohydric alcohol compound are vaporized separately, in separate vaporizing devices, and the resultant vapors are separately fed into a reactor so that the fed vapors are mixed in the reactor to form a feed gas. In this embodiment, the active catalyst component may be previously impregnated in the inert solid carrier consisting of a number of inert solid grains.

In the above-mentioned embodiments, the vaporization device or devices are located outside or inside the reactor.

In still another embodiment of the present invention, the active catalyst component in a gas phase is fed together with the feed gas into the reactor containing an inert solid carrier, while allowing the inert solid carrier in the reactor to be impregnated with the fed active catalyst component to provide a catalyst. In this case, the inert solid carrier is preferably in the form of a number of solid grains.

In this embodiment, the feed gas is prepared outside or inside the reactor, and is mixed with the active catalyst component in a gas phase outside or inside reactor.

When the active catalyst component is in the state of a liquid under the ambient atmospheric condition, it is vaporized separately from the dihydric phenol compound and the monohydric alcohol compound or together with at least one of the above-mentioned compounds.

When the active catalyst component is in the state of a solid under the ambient atmospheric condition, it is dissolved in water, an organic solvent, or preferably, and the monohydric alcohol compound, the resultant solution is sprayed into the reactor through a spray nozzle arranged in the reactor, or into the vaporization device for at least one of the compounds through a spray nozzle arranged in the vaporization device.

Also, the feed gas can be intermittently mixed with an additional amount of the active catalyst component, to maintain the amount of the active catalyst component impregnated in the inert solid carrier at a predetermined level.

In the process of the present invention, the contact of the fed gas with the active catalyst component carried on the inert solid carrier is carried out at a temperature of from 200° C. to 400° C., preferably from 230° C. to 350° C., more preferably from 240° C. to 330° C. under the ambient atmospheric pressure or higher.

The dihydric phenol compound usable for the present invention is preferably selected from unsubstituted dihydric phenolic compounds, for example, catechol, hydroquinone and resorcinol; substituted dihydric phenolic compounds having at least one lower alkyl radicals with 1 to 4 carbon atoms, for example, 4-methyl catechol 2-methyl catechol and 2-methyl hydroquinone; and another substituted dihydric phenolic compound having at least one halogen atom, for example, 4-chlorocatechol, 2-chlorocatechol, and 2-chlorohydroquinone.

The lower monohydric alcohol compound usable for the present invention is preferably selected from a straight and branched aliphatic monohydric alcohol compound having preferably 1 to 6 carbon atoms, more preferably 1 to 4 carbon atoms, for example, methyl alcohol, ethyl alcohol, n-propyl alcohol, isopropyl alcohol, n-butyl alcohol, isobutyl alcohol, secondary-butyl alcohol, and tert-butyl alcohol.

In the catalyst usable for the present invention the active catalyst component comprises at least one member selected from the group consisting of phosphorus compounds, and mixtures and reaction products of phosphorus compounds with boron compounds.

The phosphorus compound usable for the present invention is preferably selected from the group consisting of orthophosphoric acid, alkyl phosphates, for example, trimethyl phosphate, dimethyl phosphate, monomethyl phosphate, triethyl phosphate, diethyl phosphate and monoethyl phosphate, pyrophosphoric acid, metaphosphoric acid, tetraphosphoric acid, polymetaphosphoric acid, and unhydrated phosphoric acid.

A most preferable phosphorus compound for the present invention is orthophosphoric acid.

The boron compound usable for the present invention is selected from the group consisting of orthoboric acid, alkyl borates, for example, trimethyl borate and triethyl borate, metaboric acid, tetraboric acid, and boron oxide.

A most preferable boron compound for the present invention is orthoboric acid.

The phosphorus compounds and the boron compounds are used in the state of a mixture or a reaction product thereof. For example, the reaction product may be boron phosphate ($BPO_4$) produced from the above-mentioned phosphorus compounds and boron compounds.

In the active catalyst component, preferably the atomic ratio of the phosphorus (P) to boron (B) is from 1:0 to 1:10, more preferably from 1:0 to 1:5, still more preferably from 1:0 to 1:2.

In the catalyst usable for the present invention, the inert solid carrier is impregnated with the active catalyst component. The inert solid carrier is composed of an inert porous solid material which, preferably, substantially does not cause the dihydric phenolic compound, the monohydric alcohol compound and the resultant monoalkylether of the dihydric phenol compound to be modified, and can be impregnated with or carry thereon the active catalyst component to form a fixed catalyst bed (a catalyst-filled stratum) or a movable catalyst bed, Also, the inert solid carrier preferably has a pore volume of 0.1 ml/g or more, more preferably 0.2 ml/g or more, and a specific surface area (BET surface area) of 1 m$^2$/g or more, more preferably 5 m$^2$/g or more.

Further, the inert solid carrier is preferably in the form of a number of solid grains. The inert solid grains preferably have an average size of 1 to 10 mm, more preferably 2 to 8 mm. The inert solid grains may be in the shape of rod-shaped pellets, annular pellets, spheres or amorphous particles. The inert solid carrier may be in the form of files or fibrils, for example asbesto fibrils.

The inert solid carrier usable for the present invention preferably comprises at least one member selected from the group consisting of α-alumina, θ-alumina-containing α-alumina, γ-alumina, activated carbon, titania, silica-alumina, zeolite, kaolin, bentonite, and acid clay.

When a reactor is filled by a number of catalyst grains each comprising an inert solid carrier grain impregnated with an active catalyst component, the catalyst grains preferably have an average size of 1 to 10 mm, more preferably 2 to 8 mm, and are filled at a filling density of from 0.8 to 1.2 g/ml, and a porosity of 30 to 35%.

Where used in a moving bed reactor, the catalyst grains preferably have an average size of 0.1 to 5 mm, more preferably 0.5 to 3 mm.

In the catalyst grains, the inert solid carrier preferably comprise aluminum oxide having an α-type crystalline structure, i.e., α-alumina. The α-alumina may contain a small amount of θ type aluminum oxide wherein.

The inert alumina preferably is in the form of a number of particles having an average size of 1 to 10 mm, more preferably 2 to 8 mm, or in the form of tablets having a major axis of 1 to 10 mm.

The α-alumina is prepared by a heat treatment at a higher temperature than that necessary for the other types of alumina, and thus is chemically most inert and chemically and thermally most stable. The crystalline structure of the α-alumina can be confirmed by the X-ray diffractometric method disclosed in "Catalyst Engineering Course, Vol. 10, page 27 (1977), Handbook for Element-Classified Catalysts, published by Chijin Shokan".

In the catalyst grains consisting of inert solid α-alumina grains and an active catalyst component carried on the α-alumina grains, the active catalyst component preferably has a atomic ratio of boron (B) to phosphorus (P) of from 1:0.1 to 1:1.5, more preferably from 1:0.2 to 1:1.2, and the content of the active catalyst component is from about 2 to 50% by weight, more preferably from 5 to 40% by weight, in terms of the sum of $B_2O_3$ and $P_2O_5$, based on the entire weight of the catalyst grains.

Preferably, the catalyst grains is prepared in such a manner that an active catalyst component is prepared by mixing the boron compound with the phosphorus compound, in a predetermined composition; the mixture is dissolved in water in an amount of about 0.2 to 5 times, preferably 0.2 to 4 times the weight of the mixture, to provide an active catalyst component solution; a predetermined amount of inert α-alumina grains is immersed in the active catalyst component solution; the resultant active catalyst component solution-immersed α-alumina grains are heat stirred at a temperature of from 50° C. to 150° C., preferably from 70° C. to 120° C., for 2 to 30 hours and then dried; and the above-mentioned immersing, heat stirring and drying operations are repeated several times.

The resultant catalyst grains are calcined in air at a temperature of 200° C. to 600° C., for 1 to 10 hours, if necessary.

In an embodiment of the process of the present invention, a feed comprising a dihydric phenol compound and a monohydric alcohol compound is brought into contact with the active catalyst component carried on the α-alumina grains at a temperature of from 200° C. to 400° C., preferably 230° C. to 350° C., more preferably 240° C. to 330° C., under the ambient atmospheric pressure or higher whereby the dihydric phenol compound reacts with the monohydric phenol compound in a gas phase to produce a monoalkylether of the phenol compound. Then the resultant reaction mixture gas is cooled to collect the reaction product comprising the monoalkylether of the phenol compound.

The cooling temperature is not critical as long as the reaction product can be liquefied at that temperature under the ambient atmospheric pressure. Usually, the reaction mixture gas is cooled to a temperature of 40° C. or less, at which the resultant reaction product can be easily handled.

In the above-mentioned embodiment, the dihydric phenol compound is usually fed in a feed rate of from 0.01 to 1.0 g/hr, preferably from 0.05 to 0.5 g/hr, per cm$^3$ of the catalyst.

Also, the monohydric alcohol compound is usually fed in an amount of 1 to 50 moles, preferably 2 to 10 moles per mole of the dihydric phenol compound.

In another embodiment of the process of the present invention, a mixture gas of a dihydric phenol compound and a monohydric alcohol compound with an active catalyst component comprising at least one member selected from phosphorus compounds and mixtures and reaction products of phosphorus compound and boron compound, is introduced into a reactor containing an inert solid carrier, while allowing the inert solid carrier to be impregnated with the active catalyst component.

After the start of the introduction of the mixture gas into the reactor, the conversion of the dihydric phenol compound gradually increases with an increase in the amount of the active catalyst component impregnated in the inert solid carrier, and when the amount of the active catalyst component carried on the inert solid carrier is equilibrated, the conversion of the dihydric phenol compound becomes constant.

When the reaction system reaches an equilibrium condition, the feed of the active catalyst component is stopped and the feed gas comprising only the dihydric phenol compound and the monohydric alcohol component is fed to the reactor for a certain time, as long as the conversion of the dihydric phenol compound is maintained at a satisfactorily high level, because the penetration and impregnation of the active catalyst component into the inert solid carrier is effected rapidly, but the removal of the impregnated active catalyst component from the inert solid carrier is carried out very slowly.

When the conversion of the dihydric phenol compound approaches a lower limit of the satisfactory range thereof, an additional amount of the active catalyst component is fed together with the feed gas into the reactor to maintain the conversion of the dihydric phenol compound within the satisfactory range.

Namely, in the embodiment of the process of the present invention, the feed gas can be intermittently mixed with an additional amount of the active catalyst component, to maintain the amount of the active catalyst component impregnated in the inert solid carrier and to control the amount of the active catalyst compound impregnated in the inert solid carrier.

Also, the feed gas can be continuously mixed with the active catalyst component in an amount necessary to maintain the amount of the active catalyst component impregnated in the inert solid carrier constant.

When the active catalyst component is fed in a gas phase together with the feed gas into the reactor containing therein the inert solid carrier, a major portion of the fed active catalyst component is impregnated in the inert solid carrier and the remaining portion of the active catalyst component passes straight through the reactor and is introduced into the cooling device, and is dissolved in the cooled reaction product liquid. Therefore, the amount of the active catalyst component to be fed into the reactor should be strictly controlled to an appropriate level, to prevent an uneconomical consumption thereof. Also, the amount of the active catalyst component dissolved in the reaction product should be eliminated and recovered, whereas the active catalyst component dissolved in the reaction product does not affect the resultant monoalkylether of the dihydric phenol compound.

The feed gas containing the active catalyst component is brought into contact with the active catalyst component carried on the inert solid carrier at a temperature of 200° C. to 400° C., preferably 230° C. to 350° C., more preferably 240° C. to 330° C., under the ambient atmospheric pressure or higher.

The resultant reaction mixture gas discharged from the reactor is treated in the same manner as mentioned above, to collect the resultant monoalkylether of the dihydric phenol compound.

In the above-mentioned embodiment, the dihydric phenol compound is usually fed at the same feed rate as mentioned above, and the monohydric alcohol compound is fed in the same amount as mentioned above, to the reactor.

The resultant monoalkylethers of the dihydric phenol compound, for example, guaiacol, catechol ethylether and hydroquinone monomethylether, are useful as intermediates of various perfumes, medicines, and antioxidants, and as stabilizers for synthetic resins.

EXAMPLES

The present invention will be further illustrated by way of specific examples, which are representative and do not restrict the scope of the present invention in any way.

EXAMPLE 1

1) Preparation of catalyst grains

A four-necked separable flask equipped with a stirrer, a thermometer, a dropping funnel, and a cooling tube was charged with a mixture of 15.5 g (0.25 moles) of $H_3BO_3$ and 90 g of water, the resultant solution in the flask was heated to a temperature of 100° C., and then while stirring the $H_3BO_3$ solution at the above-mentioned temperature, an aqueous solution of 28.8 g (0.25 moles) of a 85% by weight $H_3PO_4$ was gradually dropped into the $H_3PO_3$ solution over about one hour. The resultant reaction mixture was then stirred for 20 hours while maintaining the temperature thereof at 100° C., and finally, the reaction mixture was cooled and then diluted with water to provide 200 g of an aqueous solution of $BPO_4$.

The $BPO_4$ solution in an amount of 25 g was mixed with 50 ml (47 g) of $\alpha$-alumina grains (available under the trademark of AM-S34 from Fujimi Kenmazai Kogyo K.K.) having an average particle size of 1 mm, a specific surface area of 7.2 $m^2/g$ and a pore volume of 0.36 $cm^3/g$, and the resultant mixture was dried on a hot plate. The dried grains were mixed with 25 g of the same $BPO_4$ solution as that mentioned above, the resultant mixture was dried on a hot plate, and the dried grains then sintered at a temperature of 400° C. for 4 hours.

The resultant catalyst grains contained an active catalyst component consisting of $BPO_4$ in a content of 14% by weight.

2) Etherifying reaction

A refractory glass reaction tube having an inside diameter of 30 mm and a length of 500 mm was charged with 25 ml (26.9 g) of the above-mentioned catalyst grains at a bulk specific gravity of 1.08, to form a catalyst grain stratum, and glass beads for preheating and having a diameter of 2 mm were then placed on the catalyst grain stratum at a bulk specific gravity of 1.52. The temperature of the charge in the reaction tube was raised to about 270° C. while flowing nitrogen gas therethrough, a solution of 50 parts by weight of catechol in 50 parts by weight of methyl alcohol was vaporized, and the resultant feed gas was continuously fed into the reaction tube at a feed rate of 15 ml/hr for 44 hours under the ambient atmospheric pressure. The resultant reaction mixture comprising guaiacol was cooled to a temperature of 20° C., and the liquefied guaiacol was collected.

At two stages of 4 hours and 44 hours after the start of the feed of the feeding gas, the composition of the resultant reaction mixture was analyzed by gas chromatography, and the conversion of catechol, the selectivity of guaiacol, the selectivity of veratrol, and the selectivity of other by-products were determined from the results of the analysis.

These results are shown in Table 1.

TABLE 1

| Item | Reaction time | |
|---|---|---|
| | 4 hours | 44 hours |
| Conversion of catechol (%) | 31.2 | 29.3 |
| Selectivity of guaiacol (%) | 99.5 | 99.3 |
| Selectivity of veratrol (%) | 0.2 | 0.2 |
| Selectivity of other by-products (%) | 0.3 | 0.5 |

The catalyst grains exhibited a crushing strength of 1.7 kg/grain before and 44 hours after the start of the reaction, i.e., no lowering of the crushing strength of the catalyst grains due to the etherifying reaction occurred.

EXAMPLE 2

1) Preparation of catalyst grains

The same procedures for the preparation of catalyst grains as in Example 1 were carried out, except that the impregnation operation of the α-alumina grains with the $BPO_4$ aqueous solution was repeated four times.

The resultant catalyst grains contained the active catalyst component in an amount of 28% by weight in terms of $BPO_4$.

2) Etherifying reaction

The same etherifying procedures as in Example 1 were carried out, except that the catalyst grains were employed in an amount of 25 ml (30.9 g) and the reaction time was 56 hours.

The resultant reaction mixtures collected at the stages of 2 hours and 56 hours after the start of the feed of the feeding gas were subjected to the gas chromatographic analysis, and the results are shown in Table 2.

TABLE 2

| Item | Reaction time | |
|---|---|---|
| | 2 hours | 56 hours |
| Conversion of catechol (%) | 29.7 | 29.9 |
| Selectivity of guaiacol (%) | 98.6 | 99.3 |
| Selectivity of veratrol (%) | 0.4 | 0.3 |
| Selectivity of other by-products (%) | 1.0 | 0.4 |

The catalyst grains exhibited a crushing strength of 1.7 kg/grain at both the stages of before and 56 hours after the start of the reaction, i.e., no lowering of the crushing strength of the catalyst grains due to the etherifying reaction occurred, as in Example 1.

EXAMPLE 3

1) Preparation of catalyst grains

The same procedures for the preparation of catalyst grains as in Example 1 were carried out. 2) Etherifying reaction The same etherifying procedures as in Example 1 were carried out, except that the catechol (50% by weight)-ethyl alcohol (50% by weight) solution was fed at a feed rate of 15 ml/hr, the reaction temperature was 280° C., and the reaction time was 30 hours.

The resultant reaction mixtures collected at the stages of 2 hours and 30 hours after the start of the feed of the feeding gas were subjected to the gas chromatographic analysis, and the results are shown in Table 3.

TABLE 3

| Item | Reaction time | |
|---|---|---|
| | 2 hours | 30 hours |
| Conversion of catechol (%) | 26.3 | 29.8 |
| Selectivity of catechol ethyl ether (%) | 98.7 | 98.6 |
| Selectivity of catechol diethyl ether (%) | 0.1 | 0.1 |

TABLE 3-continued

| Item | Reaction time | |
|---|---|---|
| | 2 hours | 30 hours |
| Selectivity of other by-products (%) | 1.2 | 1.3 |

The catalyst grains exhibited a crushing strength of 1.7 kg/grain at both the stages of before and 30 hours after the start of the reaction, i.e., no lowering of the crushing strength of the catalyst grains due to the etherifying reaction occurred as in Example 1.

EXAMPLE 4

1) Preparation of catalyst grains

The same procedures for the preparation of catalyst grains as in Example 1 were carried out.

2) Etherifying reaction

The same etherifying procedures as in Example 1 were carried out, except that a hydroquinone (25% by weight)-methyl alcohol (75% by weight) solution was fed at a feed rate of 30 ml/hr, and the reaction time was 30 hours.

The resultant reaction mixtures collected at the stages of 2 hours and 30 hours after the start of the feed of the feeding gas were subjected to the gas chromatographic analysis, and the results are shown in Table 4.

TABLE 4

| Item | Reaction time | |
|---|---|---|
| | 2 hours | 30 hours |
| Conversion of hydroquinone (%) | 31.5 | 31.0 |
| Selectivity of hydroquinone monomethylether (%) | 91.8 | 92.4 |
| Selectivity of hydroquinone dimethylether (%) | 5.2 | 4.8 |
| Selectivity of other by-products (%) | 3.0 | 2.8 |

The catalyst grains exhibited a crushing strength of 1.7 kg/grain at both the stages of before and 30 hours after the start of the reaction, i.e., no lowering of the crushing strength of the catalyst grains due to the etherifying reaction occurred as in Example 1.

EXAMPLE 5

1) Preparation of catalyst grains

The same procedures for the preparation of catalyst grains as in Example 1 were carried out, except that the inert solid carrier consisted of α-alumina grains (available under the trademark of AM-S34, from Fujimi Kemmazai Kogyo K.K.) having an average grain size of 3.0 mm, a specific surface area of 7.0 m²/g, and a pore volume of 0.38 cm³/g, and the impregnation operation of the α-alumina grains with the $BPO_4$ aqueous solution was repeated 8 times.

The resultant catalyst grains contained the active catalyst component in an amount of 20.6% of weight in terms of $BPO_4$.

2) Etherifying reaction

The same etherifying procedures as in Example 1 were carried out, except that the catalyst grains were employed in an amount of 25 ml (25.0 g) and at a bulk specific gravity of 1.00, the catechol-methyl alcohol solution was fed at a feed rate of 5 ml/hr into the reaction tube while changing the reaction temperature as shown below, and the reaction time was 30 hours.

| Change of Reaction Temperature | |
| --- | --- |
| Reaction time (from start of reaction) | Reaction temperature |
| from 0 to 10 hours | 250° C. |
| from 10 hours to 20 hours | 270° C. |
| from 20 hours to 30 hours | 300° C. |

The resultant reaction mixtures collected at the stages of 10 hours, 20 hours and 30 hours after the start of the feed of the feeding gas were subjected to the gas chromatographic analysis, and the results are shown in Table 5.

TABLE 5

| | Reaction time | | |
| --- | --- | --- | --- |
| Item | 10 hours | 20 hours | 30 hours |
| Conversion of catechol (%) | 30.1 | 43.4 | 72.9 |
| Selectivity of guaiacol (%) | 98.9 | 99.0 | 97.7 |
| Selectivity of veratrol (%) | 0.37 | 0.66 | 2.00 |
| Selectivity of other by-products (%) | 0.75 | 0.32 | 0.28 |

The catalyst grains exhibited a crushing strength of 3.9 kg/grain at both the stages of before and 30 hours after the start of the reaction, i.e., no lowering of the crushing strength of the catalyst grains due to the etherifying reaction occurred as in Example 1.

EXAMPLE 6

1) Preparation of catalyst grains

The same procedures for the preparation of catalyst grains as in Example 1 were carried out, except that the inert solid carrier consisted of α-alumina grains (available under the trademark of AM-S34, from Fujimi Kemmazai Kogyo K.K.) having an average grain size of 3.0 mm, a specific surface area of 5.6 m$^2$/g and a pore volume of 0.34 cm$^3$/g, and the 85% by weight $H_3PO_4$ aqueous solution was added dropwise to the $H_3BO_3$ aqueous solution. The amount of the $H_3PO_4$ aqueous solution was varied at five levels to provide five types of catalyst grains a, b, c, d, and e as shown in the following table, in which the amounts of the phosphoric acid in terms of $P_2O_5$ and the amounts of the boric acid in terms of $B_2O_3$ in the resultant active catalyst component carried on the α-alumina grains, and the atomic ratio P/B of the active catalyst component, are shown.

| | Composition of active catalyst component | | |
| --- | --- | --- | --- |
| Type of catalyst | $P_2O_5$ (g)(*)$_1$ | $B_2O_3$ (g)(*)$_1$ | Atomic ratio P/B |
| a | 10.7 | 4.4 | 1.2 |
| b | 8.9 | 4.4 | 1.0 |
| c | 7.1 | 4.4 | 0.8 |
| d | 3.6 | 4.4 | 0.4 |
| e | 1.8 | 4.4 | 0.2 |

Note: (*)$_1$ The amounts in grams of $P_2O_5$ and $B_2O_3$ are based on 100 ml of the catalyst grains.

2) Etherifying reaction

The same etherifying procedures as in Example 1 were carried out, except that one member of the catalyst grains a, b, c, d, and e were employed in an amount of 25 ml and the reaction time was 8 hours.

The resultant reaction mixtures collected at the stages of 8 hours after the start of the feed of the feeding gas were subjected to the gas chromatographic analysis, and the results are shown in Table 6.

TABLE 6

| | Item | |
| --- | --- | --- |
| Item | Type of catalyst | Reaction time 8 hours |
| Conversion of catechol (%) | a | 25.5 |
| | b | 27.0 |
| | c | 29.5 |
| | d | 31.9 |
| | e | 27.9 |
| Selectivity of guaiacol (%) | a | 99.6 |
| | b | 99.4 |
| | c | 99.5 |
| | d | 99.6 |
| | e | 99.5 |
| Selectivity of veratrol (%) | a | 0.22 |
| | b | 0.18 |
| | c | 0.25 |
| | d | 0.22 |
| | e | 0.22 |
| Selectivity of other by-products (%) | a | 0.21 |
| | b | 0.40 |
| | c | 0.19 |
| | d | 0.20 |
| | e | 0.30 |

COMPARATIVE EXAMPLE 1

1) Preparation of Catalyst grains

The same procedures for the preparation of catalyst grains as the catalyst (e) of Example 9 were carried out, except that the 85% by weight $H_3PO_4$ aqueous solution was not added dropwise to the $HBO_3$ aqueous solution, and thus the atomic ratio (P/B) of the active catalyst component was 0.

The resultant catalyst grains contained the active catalyst component in an amount of 4.4 g in terms of $B_2O_3$ per 100 ml of the catalyst grains.

2) Etherifying reaction

The same etherifying procedures as in Example 9 were carried out except that the above-mentioned catalyst grains were employed in an amount of 25 ml.

The resultant reaction mixtures collected at the stages of 8 hours after the start of the feed of the feeding gas were subjected to the gas chromatographic analysis, and the results are shown in Table 7.

TABLE 7

| Item | Reaction time 8 hours |
| --- | --- |
| Conversion of catechol (%) | 1.1 |
| Selectivity of guaiacol (%) | 98.9 |
| Selectivity of velatrol (%) | 0.0 |
| Selectivity of other by-products (%) | 1.1 |

EXAMPLE 7

The same refractory glass reaction tube as mentioned in Example 1 was charged with 25 ml (24.34 g) of an inert solid carrier consisting of α-alumina grains having an average size of 3 mm, a pore volume of 0.33 ml/g and a specific surface area of 11.2 m$^2$/g, and then 90 ml of glass beads for preheating and having an average diameter of 2 mm were placed at a bulk specific gravity of 1.52 on the α-alumina grain stratum.

The charge in the reaction tube was heated at a temperature of 280° C. in the center portion of the α-alumina grain stratum, while flowing nitrogen gas through the reaction tube, a solution of 100.0 g of catechol and 1.10 g of 85% by weight phosphoric acid in 98.9 g of methyl alcohol was vaporized, and the resultant feed gas containing phosphoric acid was continuously fed at a feed rate of 10.55 g/hr (LHSV: 0.21 g/ml.hr) into the reaction tube for 8 hours, to prepare guaiacol by the reaction of catechol with methyl alcohol.

The resultant reaction mixture gas was cooled to a temperature of 20° C., to collect a reaction product liquid comprising guaiacol.

The resultant reaction product liquids collected every 2 hours after the start of the reaction were subjected to a gas chromatographic analysis to determine the amounts of the reaction products.

Then, the conversion of catechol (CL), the selectivity of guaiacol (GCL), the selectivity of veratrol (VL) and the selectivity of the other by-products (OTH), for example, methylated cyclic compounds were calculated from the analysis results.

These results are shown in Table 8.

TABLE 8

| Reaction time (hr) from start of reaction | Conversion of CL (%) | Selectivity (%) | | |
|---|---|---|---|---|
| | | GCL | VL | OTH |
| 2 | 15.34 | 99.70 | 0.20 | 0.10 |
| 4 | 28.08 | 99.39 | 0.44 | 0.16 |
| 6 | 34.07 | 99.21 | 0.52 | 0.28 |
| 8 | 39.16 | 99.11 | 0.57 | 0.32 |

EXAMPLE 8

The same refractory glass reaction tube having an inside diameter of 26 mm and a length of 500 mm as in Example 1 was charged with 18 ml (15.43 g) of an inert solid carrier consisting of α-alumina grains having an average size of 3 mm, a pore volume of 0.30 ml/g and a specific surface area of 7.0 m$^2$/g, and then 70 ml of glass beads for preheating and having a diameter of 2 to 4 mm were placed at a bulk specific gravity of 1.52 on the α-alumina grain stratum.

Three types of feed solutions A, B, and C having the compositions as shown in Table 9 were prepared and vaporized.

TABLE 9

| Composition Component | Composition (part by weight) | | |
|---|---|---|---|
| | Type A | Type B | Type C |
| Catechol | 100 | 100 | 100 |
| Methyl alcohol | 98.32 | 96.64 | 99.16 |
| Orthoboric acid | 0.58 | 1.16 | 0.29 |
| 85% phosphoric acid | 1.10 | 2.20 | 0.55 |

The feed gasses A, B and C were fed into the reaction tube at the stages as shown in Table 10, at the feed rate (LHSV) as shown in Table 10, and at the temperature a shown in Table 10.

TABLE 10

| Reaction stage from start of reaction (hour) | Type of feed gas | Feed rate (LHSV) (g/ml · hr) | Temperature of center portion of inert solid carrier stratum (°C.) |
|---|---|---|---|
| 0 to 16 | A | 0.3 | 270 |
| 17 to 24 | B | 0.3 | 270 |
| 25 to 28 | B | 0.2 | 270 |
| 29 to 32 | B | 0.3 | 300 |
| 33 to 36 | A | 0.2 | 270 |
| 37 to 40 | A | 0.2 | 300 |
| 41 to 48 | C | 0.2 | 270 |
| 49 to 56 | C | 0.2 | 300 |

The resultant reaction mixture gas was cooled to a temperature of 20° C., to collect a reaction product liquid comprising guaiacol, and the resultant reaction product liquids collected after the reaction times shown in Table 14 were subjected to the same gas chromatographic analysis as in Example 10.

The results are shown in Table 11.

TABLE 11

| Reaction time (hr) from start of reaction | Conversion of CL (%) | Selectivity (%) | | |
|---|---|---|---|---|
| | | GCL | VL | OTH |
| 4 | 15.32 | 99.95 | 0 | 0.05 |
| 8 | 20.75 | 99.65 | 0.15 | 0.20 |
| 16 | 21.23 | 99.70 | 0.15 | 0.15 |
| 24 | 19.81 | 99.59 | 0.10 | 0.31 |
| 28 | 24.39 | 99.31 | 0.20 | 0.49 |
| 32 | 35.82 | 99.33 | 0.34 | 0.34 |
| 36 | 25.57 | 99.64 | 0.24 | 0.12 |
| 40 | 44.25 | 99.23 | 0.56 | 0.21 |
| 48 | 25.14 | 99.63 | 0.25 | 0.12 |
| 56 | 44.41 | 99.37 | 0.53 | 0.10 |

EXAMPLE 9

The same refractory glass reaction tube as mentioned in Example 8 was charged with 18 ml (17.50 g) of an inert solid carrier consisting of α-alumina grains having an average size of 3 mm, a pore volume of 0.33 ml/g and a specific surface area of 11.2 m$^2$/g, and then 7 ml of glass beads for preheating and having an average diameter of 2 mm were placed at a bulk specific gravity of 1.52 on the α-alumina grain stratum.

The charge in the reaction tube was heated at a temperature of 280° C. in the center portion of the α-alumina grain stratum, while flowing nitrogen gas through the reaction tube, a solution of 100.0 g of catechol and 1.34 g of trimethyl phosphate in 98.66 g of methyl alcohol was vaporized, and the resultant feed gas containing trimethyl phosphate was continuously fed at a feed rate of 7.30 g/hr (LHSV: 0.20 g/ml.hr) into the reaction tube for 24 hours, to prepare guaiacol by the reaction of catechol with methyl alcohol.

The temperature of the center portion of the inert solid carrier stratum was raised from 280° C. to 300° C. at 16 hours after the start of the reaction, and thereafter, was maintained at 300° C. until the end of the reaction.

The resultant reaction mixture gas was cooled to a temperature of 20° C. to collect a reaction product liquid comprising guaiacol, and the resultant reaction product liquids collected every 4 hours after the start of the reaction were subjected to the same gas chromatographic analysis as in Example 8.

The results are shown in Table 12.

TABLE 12

| Reaction time (hr) from start of reaction | Conversion of CL (%) | Selectivity (%) | | |
|---|---|---|---|---|
| | | GCL | VL | OTH |
| 4 | 28.68 | 99.46 | 0.44 | 0.10 |
| 8 | 39.51 | 99.37 | 0.54 | 0.08 |
| 12 | 40.94 | 99.43 | 0.51 | 0.06 |
| 16 | 40.00 | 99.46 | 0.48 | 0.06 |
| 20 | 53.58 | 98.93 | 0.89 | 0.18 |
| 24 | 52.24 | 98.97 | 0.88 | 0.15 |

EXAMPLE 10

The same refractory glass reaction tube as mentioned in Example 7 was charged with 25 ml (12.43 g) of an inert solid carrier consisting of γ-alumina grains available under the trademark of NKH 1-24 from Sumitomo Kagaku Kogyo K.K., and having an average size of 3 mm, a pore volume of 0.90 ml/g and a specific surface area of 110 m²/g, and then 90 ml of glass beads for preheating and having an average diameter of 2 mm were placed at a bulk specific gravity of 1.52 on the γ-alumina grain stratum.

The charge in the reaction tube was heated at a temperature of 280° C. in the center portion of the γ-alumina grain stratum, while flowing nitrogen gas through the reaction tube, the same feed solution as in Example 10 was vaporized, and the resultant feed gas containing phosphoric acid was continuously fed at a feed rate of 10.20 g/hr (LHSV: 0.20 g/ml.hr) into the reaction tube for 16 hours, to prepare guaiacol by the reaction of catechol with methyl alcohol.

The resultant reaction mixture gas was cooled to a temperature of 20° C. to collect a reaction product liquid comprising guaiacol, and the resultant reaction product liquids collected every 4 hours after the start of the reaction were subjected to the same gas chromatographic analysis as in Example 6.

The results are shown in Table 13.

TABLE 13

| Reaction time (hr) from start of reaction | Conversion of CL (%) | Selectivity (%) | | |
|---|---|---|---|---|
| | | GCL | VL | OTH |
| 4 | 28.75 | 98.17 | 0.24 | 1.59 |
| 8 | 30.99 | 98.86 | 0.73 | 0.40 |
| 12 | 32.59 | 98.50 | 1.20 | 0.30 |
| 16 | 34.43 | 98.48 | 1.32 | 0.20 |

EXAMPLE 11

The same refractory glass reaction tube as mentioned in Example 8 was charged with 18 ml (14.75 g) of an inert solid carrier consisting of α-alumina grains having an average size of 3 mm, a pore volume of 0.40 ml/g and a specific surface area of 48.1 m²/g, and then 70 ml of glass beads for preheating and having an average diameter of 2 mm were placed at a bulk specific gravity of 1.52 on the α-alumina grain stratum.

The charge in the reaction tube was heated at a temperature of 270° C. in the center portion of the α-alumina grain stratum, while flowing nitrogen gas through the reaction tube, a solution of 100.0 g of catechol, 1.10 g of 85% by weight phosphoric acid, and 1.16 g of orthoboric acid in 97.74 g of methyl alcohol was vaporized, and the resultant feed gas containing the active catalyst component was continuously fed at a feed rate of 7.30 g/hr (LHSV: 0.20 g/ml.hr) into the reaction tube for 24 hours, to prepare guaiacol by the reaction of catechol with methyl alcohol. The active catalyst component had an atomic ratio B/P of boron to phosphorus of 2:1.

The temperature of the center portion of the inert solid carrier stratum was raised from 270° C. to 300° C. 16 hours after the start of the reaction, and thereafter, maintained at the above-mentioned temperature until the end of the reaction.

The resultant reaction mixture gas was cooled to a temperature of 20° C. to collect a reaction product liquid comprising guaiacol, and the resultant reaction product liquids collected every 4 hours after the start of the reaction were subjected to the same gas chromatographic analysis as mentioned in Example 7.

The results are shown in Table 14.

TABLE 14

| Reaction time (hr) from start of reaction | Conversion of CL (%) | Selectivity (%) | | |
|---|---|---|---|---|
| | | GCL | VL | OTH |
| 4 | 16.29 | 99.46 | 0.18 | 0.36 |
| 8 | 19.46 | 99.34 | 0.46 | 0.15 |
| 12 | 22.72 | 99.17 | 0.79 | 0.04 |
| 16 | 24.21 | 99.20 | 0.76 | 0.04 |
| 20 | 42.43 | 97.93 | 1.71 | 0.36 |
| 24 | 43.76 | 97.98 | 1.81 | 0.21 |

EXAMPLE 12

The same procedures as those described in Example 11 were carried out, with the following exceptions.

The feed solution was composed of 100.0 g of catechol, 98.61 g of methyl alcohol, 1.10 g of 85% by weight phosphoric acid, and 0.29 g of orthoboric acid, and the resultant active catalyst component had an atomic ratio B/P of 1:2.

The results are shown in Table 15.

TABLE 15

| Reaction time (hr) from start of reaction | Conversion of CL (%) | Selectivity (%) | | |
|---|---|---|---|---|
| | | GCL | VL | OTH |
| 4 | 20.55 | 99.56 | 0.35 | 0.09 |
| 8 | 24.71 | 99.49 | 0.55 | — |
| 12 | 29.31 | 98.20 | 0.82 | 0.98 |
| 16 | 31.42 | 98.66 | 0.96 | 0.38 |
| 20 | 51.69 | 97.87 | 1.91 | 0.22 |
| 24 | 54.25 | 97.64 | 2.15 | 0.22 |

EXAMPLE 13

The same procedures as those described in Example 9 were carried out with the following exceptions.

The feed solution was composed of 100.0 g of catechol, 99.15 g of methyl alcohol, and 0.85 g of pyrophosphoric acid.

The results are shown in Table 16.

TABLE 16

| Reaction time (hr) from start of reaction | Conversion of CL (%) | Selectivity (%) | | |
|---|---|---|---|---|
| | | GCL | VL | OTH |
| 4 | 25.86 | 99.57 | 0.37 | 0.06 |
| 8 | 34.89 | 99.41 | 0.50 | 0.09 |
| 12 | 38.29 | 99.33 | 0.54 | 0.13 |
| 16 | 37.94 | 99.50 | 0.42 | 0.08 |
| 20 | 51.73 | 99.05 | 0.80 | 0.15 |
| 24 | 53.40 | 99.16 | 0.69 | 0.15 |

EXAMPLE 14

The same refractory glass reaction tube as mentioned in Example 1 was charged with 25 ml (13.83 g) of an inert solid carrier consisting of activated carbon grains (available under the trademark of Kureha Beads, from Kureha Kagaku Kogyo K.K.) having a size of 0.3 to 0.9 mm, a pore volume of 0.70 ml/g and a specific surface area of 1100 m²/g, and then 90 ml of glass beads for preheating and having an average diameter of 2 mm were placed at a bulk specific gravity of 1.52 on the activated carbon grain stratum.

The charge in the reaction tube was heated at a temperature of 280° C. in the center portion of the inert solid carrier stratum while flowing nitrogen gas through the reaction tube, a solution of 100.0 g of catechol and 1.10 g of 85% by weight phosphoric acid in 98.9 g of methyl alcohol was vaporized, and the resultant feed gas containing phosphoric acid was continuously fed at a feed rate of 10 g/hr (LHSV: 0.20 g/ml.hr) into the reaction tube for 8 hours, to prepare guaiacol by the reaction of catechol with methyl alcohol. Then, the temperature of the center portion of the inert solid carrier stratum was dropped from 280° C. to 260° C. at 8 hours after the start of the reaction, and the feed rate of the feed gas was raised to 15 g/hr (LHSV: 0.30 g/ml.hr) at 16 hours after the start of the reaction. The reaction was stopped 24 hours after the start of the reaction.

The resultant reaction mixture gas was cooled to a temperature of 20° C. to collect a reaction product liquid comprising guaiacol, and the resultant reaction product liquids collected at the stages of every 4 hours after the start of the reaction were subjected to the same gas chromatographic analysis as mentioned in Example 7.

The results are shown in Table 17.

TABLE 17

| Reaction time (hr) from start of reaction | Conversion of CL (%) | Selectivity (%) | | |
|---|---|---|---|---|
| | | GCL | VL | OTH |
| 4 | 63.50 | 92.77 | 6.54 | 0.69 |
| 8 | 82.91 | 86.24 | 11.31 | 2.45 |
| 12 | 65.19 | 92.29 | 6.67 | 1.04 |
| 16 | 65.23 | 92.75 | 6.40 | 0.85 |
| 20 | 33.95 | 97.51 | 2.02 | 0.47 |
| 24 | 28.71 | 97.91 | 1.50 | 0.59 |

EXAMPLE 15

The same refractory glass reaction tube as mentioned in Example 11 was charged with 18 ml (16.31 g) of an inert solid carrier consisting of titania grains (available under the trademark of Titan Beads, from Shokubai Kasei Kogyo K.K.) having a 8 to 10 mesh size, a pore volume of 0.28 ml/g and a specific surface area of 65 $m^2/g$, and then 70 ml of glass beads for preheating and having an average diameter of 2 mm were placed at a bulk specific gravity of 1.52 on the inert solid carrier stratum.

The charge in the reaction tube was heated at a temperature of 280° C. in the center portion of the titania grain stratum, while flowing nitrogen gas through the reaction tube, the same feed solution as mentioned in Example 10 was vaporized, and the resultant feed gas containing phosphoric acid was continuously fed at a feed rate of 7.2 g/hr (LHSV: 0.20 g/ml.hr) into the reaction tube for 16 hours, to prepare guaiacol by the reaction of catechol with methyl alcohol.

The resultant reaction mixture gas was cooled to a temperature of 20° C. to collect a reaction product liquid comprising guaiacol, and the resultant reaction product liquids collected at the stages as indicated in Table 18 were subjected to the same gas chromatographic analysis as mentioned in Example 7.

The results are shown in Table 18.

TABLE 18

| Reaction time (hr) from start of reaction | Conversion of CL (%) | Selectivity (%) | | |
|---|---|---|---|---|
| | | GCL | VL | OTH |
| 2 | 16.77 | 97.39 | 0.22 | 2.39 |
| 4 | 27.14 | 98.31 | 0.21 | 1.48 |
| 6 | 35.11 | 98.60 | 0.22 | 1.18 |
| 8 | 39.94 | 98.52 | 0.25 | 1.22 |
| 12 | 50.97 | 98.00 | 0.34 | 1.65 |

TABLE 18-continued

| Reaction time (hr) from start of reaction | Conversion of CL (%) | Selectivity (%) | | |
|---|---|---|---|---|
| | | GCL | VL | OTH |
| 16 | 54.34 | 97.71 | 0.39 | 1.89 |

COMPARATIVE EXAMPLE 2

The same procedures as those described in Example 7 were carried out, with the following exceptions.

The feed solution was composed of 100.0 g of catechol, 99.42 g of methyl alcohol, and 0.58 g of orthoboric acid; the feed gas was fed at a feed rate of 10.60 g/hr (LHSV: 0.20 g/ml.hr); the feeding of the feed gas was continued for 6 hours, and the gas chromatographic analysis was applied to the reaction product collected at 2 hours and 6 hours after the start of the reaction.

The results are shown in Table 19.

TABLE 19

| Reaction time (hr) from start of reaction | Conversion of CL (%) | Selectivity (%) | | |
|---|---|---|---|---|
| | | GCL | VL | OTH |
| 2 | 0 | — | — | — |
| 6 | 0 | — | — | — |

COMPARATIVE EXAMPLE 3

The same procedures as those described in Example 7 were carried out, with the following exceptions.

The same reaction tube as mentioned in Example 8 was employed; the reaction tube was filled with 100 ml of glass beads having a diameter of 2 to 4 mm, a pore volume of less than 0.1 ml/g or less, and a specific surface area of less than 1.0 $m^2/g$ the feed gas was fed at a feed rate of 7.30 g/hr (LHSV: 0.04 g/ml.hr); the feeding time of the feed gas was 4 hours.

The results are shown in Table 20.

TABLE 20

| Reaction time (hr) from start of reaction | Conversion of CL (%) | Selectivity (%) | | |
|---|---|---|---|---|
| | | GCL | VL | OTH |
| 2 | 0 | — | — | — |
| 4 | 0 | — | — | — |

COMPARATIVE EXAMPLE 4

The same procedures as those described in Example 7 were carried out, with the following exceptions.

The inert solid carrier consisted of silicon carbide grains having an average size of 3 mm and a specific surface area of 1 $m^2/g$ or less; the feed rate of the feed gas was 10.2 g/hr (LHSV: 0.20 g/ml.hr); the reaction time was 4 hours; and the analysis was applied to a reaction product collected at 4 hours after the start of the reaction.

The results are shown in Table 21.

TABLE 21

| Reaction time (hr) from start of reaction | Conversion of CL (%) | Selectivity (%) | | |
|---|---|---|---|---|
| | | GCL | VL | OTH |
| 4 | 0 | — | — | — |

COMPARATIVE EXAMPLE 5

The same procedures as those described in Comparative Example 4 were carried out, with the following exceptions.

The silicon carbide grains were replaced by α-alumina grains having an average size of 3 mm and a specific surface area of less than 1 m²/g or less, in an amount of 25 ml (39.41 g), and the analysis was applied to the reaction product collected at 5 hours and 8 hours after the start of the reaction.

The results are shown in Table 22.

TABLE 22

| Reaction time (hr) from start of reaction | Conversion of CL (%) | Selectivity (%) | | |
|---|---|---|---|---|
| | | GCL | VL | OTH |
| 5 | 5.62 | 99.72 | 0 | 0.28 |
| 8 | 6.02 | 99.72 | 0 | 0.26 |

EXAMPLE 16

The same refractory glass reaction tube as mentioned in Example 1 was charged with 37.5 ml (31.97 g) of an inert solid carrier consisting of α-alumina grains having an average size of 3 mm, a pore volume of 0.4 ml/g and a specific surface area of 48.1 m²/g, and then 90 ml of glass beads for preheating and having a diameter of 2 to 4 mm were placed at a bulk specific gravity of 1.52 on the α-alumina grain stratum.

Three types of feed gases D, E, and F having the compositions as shown in Table 26 were fed into the reaction tube at the stages as shown in Table 23.

TABLE 23

| | Type Feed gas | | |
|---|---|---|---|
| Component | Type D | Type E | Type F |
| Catechol (g) | 1000.0 | 1000.0 | 1000.0 |
| Methyl alcohol (g) | 990.0 | 995.0 | 1000.0 |
| 85% phosphoric acid (g) | 7.22 | 3.61 | 0 |
| Orthoboric acid (g) | 3.88 | 1.94 | 0 |
| Content of active catalyst component in terms of BPO₄ (% by wt.) | 0.5 | 0.25 | 0 |

The reaction tube was placed in an electric furnace having an inside diameter of 40 mm and a length of 300 mm, and the temperature of the center portion of the inert solid carrier layer was controlled to the levels as indicated in Table 24, at the conditions as indicated in Table 24, while flowing nitrogen gas at a flow rate of 20 ml/min through the reaction tube.

Each feed gas was continuously fed at the feed rate as indicated in Table 24.

TABLE 24

| Reaction stage from start of reaction (hour) | Type of feed gas | Feed rate | | Temperature of center portion of inert solid carrier layer (°C.) |
|---|---|---|---|---|
| | | (g/hr) | LHSV (g/ml · hr) | |
| 0 to 65 | D | 12.8 | 0.17 | 280 |
| 66 to 88 | E | 12.8 | 0.17 | 280 |
| 89 to 161 | E | 12.8 | 0.17 | 270 |
| 162 to 209 | E | 12.8 | 0.17 | 260 |
| 210 to 838 | E | 12.8 | 0.17 | 260 |
| 839 to 1381 | F | 7.5 | 0.10 | 260 |
| 1382 to 1645 | F | 7.5 | 0.10 | 270 |
| 1645 to 2294 | E | 7.5 | 0.10 | 270 |
| 2295 to 2438 | E | 7.5 | 0.10 | 275 |

TABLE 24-continued

| Reaction stage from start of reaction (hour) | Type of feed gas | Feed rate | | Temperature of center portion of inert solid carrier layer (°C.) |
|---|---|---|---|---|
| | | (g/hr) | LHSV (g/ml · hr) | |
| 2439 to 2474 | E | 7.5 | 0.10 | 280 |

The resultant reaction mixture gas was cooled to a temperature of 20° C. to collect a reaction product liquid comprising guaiacol, and the resultant reaction product liquids collected at the stages as shown in Table 25 were subjected to the same gas chromatographic analysis as mentioned in Example 1.

Then, the conversion of catechol (CL), the selectivity of guaiacol (GCL), the selectivity of veratrol (VL) and the selectivity of the other by-products (OTH), for example, methylated cyclic compounds were calculated from the results of the analysis.

These results are shown in Table 25 an din FIG. 1.

TABLE 25

| Reaction time (hr) from start of reaction | Conversion of CL (%) | Selectivity (%) | | |
|---|---|---|---|---|
| | | GCL | VL | OTH |
| 17 | 37.00 | 98.63 | 1.12 | 0.25 |
| 41 | 46.47 | 98.46 | 1.54 | — |
| 65 | 57.49 | 98.39 | 1.55 | 0.06 |
| 89 | 58.36 | 97.93 | 2.02 | 0.05 |
| 137 | 49.85 | 98.40 | 1.60 | — |
| 161 | 51.09 | 98.38 | 1.59 | 0.03 |
| 185 | 42.74 | 98.81 | 1.19 | — |
| 209 | 39.88 | 98.84 | 1.16 | — |
| 233 | 49.54 | 98.55 | 1.45 | — |
| 257 | 47.86 | 98.57 | 1.43 | — |
| 303 | 47.37 | 98.54 | 1.45 | 0.01 |
| 329 | 47.06 | 98.58 | 1.42 | — |
| 353 | 47.00 | 98.52 | 1.46 | 0.02 |
| 377 | 48.20 | 98.61 | 1.39 | — |
| 401 | 47.77 | 98.60 | 1.40 | — |
| 425 | 44.41 | 98.64 | 1.36 | — |
| 473 | 43.69 | 98.65 | 1.35 | — |
| 497 | 45.09 | 98.69 | 1.31 | — |
| 521 | 44.49 | 98.71 | 1.29 | — |
| 545 | 45.65 | 98.64 | 1.36 | — |
| 569 | 44.24 | 98.67 | 1.33 | — |
| 641 | 45.32 | 98.70 | 1.30 | — |
| 665 | 43.59 | 98.72 | 1.28 | — |
| 713 | 43.88 | 98.71 | 1.27 | 0.02 |
| 761 | 43.83 | 98.75 | 1.20 | 0.05 |
| 809 | 42.01 | 98.86 | 1.14 | — |
| 838 | 42.19 | 98.83 | 1.17 | — |
| 862 | 42.53 | 98.60 | 1.38 | 0.02 |
| 903 | 43.15 | 98.53 | 1.44 | 0.03 |
| 974 | 39.70 | 98.52 | 1.44 | 0.04 |
| 1022 | 39.57 | 98.49 | 1.45 | 0.06 |
| 1070 | 39.69 | 98.59 | 1.36 | 0.05 |
| 1142 | 37.16 | 98.49 | 1.46 | 0.05 |
| 1190 | 36.20 | 98.63 | 1.32 | 0.05 |
| 1238 | 38.15 | 98.49 | 1.46 | 0.05 |
| 1310 | 37.18 | 98.57 | 1.37 | 0.06 |
| 1358 | 36.63 | 98.58 | 1.35 | 0.07 |
| 1382 | 37.24 | 98.55 | 1.37 | 0.08 |
| 1406 | 42.76 | 98.10 | 1.86 | 0.04 |
| 1478 | 45.67 | 98.14 | 1.81 | 0.05 |
| 1526 | 38.51 | 98.38 | 1.57 | 0.05 |
| 1574 | 37.85 | 98.51 | 1.43 | 0.06 |
| 1646 | 35.41 | 98.72 | 1.21 | 0.07 |
| 1670 | 45.65 | 98.79 | 1.19 | 0.02 |
| 1694 | 46.43 | 98.73 | 1.23 | 0.04 |
| 1741 | 45.37 | 98.67 | 1.30 | 0.03 |
| 1766 | 45.22 | 98.64 | 1.34 | 0.02 |
| 1814 | 42.99 | 98.64 | 1.33 | 0.02 |
| 1886 | 43.38 | 98.70 | 1.28 | 0.02 |
| 1934 | 43.12 | 98.80 | 1.18 | 0.02 |
| 1982 | 42.58 | 98.83 | 1.16 | 0.01 |
| 2054 | 42.13 | 98.81 | 1.17 | 0.02 |
| 2102 | 39.85 | 98.91 | 1.08 | 0.01 |

TABLE 25-continued

| Reaction time (hr) from start of reaction | Conversion of CL (%) | Selectivity (%) | | |
|---|---|---|---|---|
| | | GCL | VL | OTH |
| 2151 | 41.84 | 98.73 | 1.26 | 0.02 |
| 2223 | 41.35 | 98.83 | 1.16 | 0.01 |
| 2271 | 41.69 | 98.78 | 1.18 | 0.04 |
| 2295 | 39.88 | 98.82 | 1.16 | 0.02 |
| 2319 | 42.38 | 98.74 | 1.24 | 0.02 |
| 2391 | 40.79 | 98.80 | 1.17 | 0.03 |
| 2439 | 39.65 | 98.85 | 1.14 | 0.01 |
| 2474 | 42.22 | 98.72 | 1.26 | 0.02 |

EXAMPLE 17

The same refractory glass reaction tube as mentioned in Example 1 was charged with 25 ml (21.47 g) of an inert solid carrier consisting of α-alumina grains having an average size of 3 mm, a pore volume of 0.30 ml/g and a specific surface area of 7.0 m$^2$/g, and then 90 ml of glass beads for preheating and having a diameter of 2 to 4 mm were placed at a bulk specific gravity of 1.52 on the α-alumina grain stratum.

Two types of feed gases G and H having the composition as indicated in Table 26 were employed.

TABLE 26

| Component | Type Feed gas | |
|---|---|---|
| | Type G | Type H |
| Catechol (g) | 1000.0 | 1000.0 |
| Methyl alcohol (g) | 996.39 | 1000.0 |
| 85% phosphoric acid (g) | 3.61 | 0 |

The reaction tube was placed in an electric furnace having an inside diameter of 40 mm and a length of 300 mm, and the temperature of the center portion of the inert solid carrier stratum was controlled to the levels as indicated in Table 27, and the feed gas of the type as indicated in Table 27 was fed into the reaction tube at the feed rate and at the stage as indicated in Table 27, while flowing nitrogen gas at a flow rate of 20 ml/min through the reaction tube.

TABLE 27

| Reaction stage from start of reaction (hour) | Type of feed gas | Feed rate | | Temperature of center portion of inert solid carrier stratum (°C.) |
|---|---|---|---|---|
| | | (g/hr) | LHSV (g/ml · hr) | |
| 0 to 21 | G | 8.5 | 0.17 | 260 |
| 22 to 69 | G | 6.0 | 0.12 | 260 |
| 70 to 189 | G | 5.0 | 0.10 | 270 |
| 190 to 525 | G | 5.0 | 0.10 | 280 |
| 526 to 621 | H | 5.0 | 0.10 | 280 |
| 622 to 861 | G | 5.0 | 0.10 | 280 |

The resultant reaction mixture gas was cooled to a temperature of 20° C. to collect a reaction product liquid comprising guaiacol, and the resultant reaction product liquids collected at the stages as shown in Table 28 were subjected to the same gas chromatographic analysis as mentioned in Example 1.

Then, the conversion of catechol (CL), the selectivity of guaiacol (GCL), the selectivity of veratrol (VL) and the selectivity of the other by-products, (OTH), for example, methylated cyclic compounds were calculated from the results of the analysis.

Figure 2:
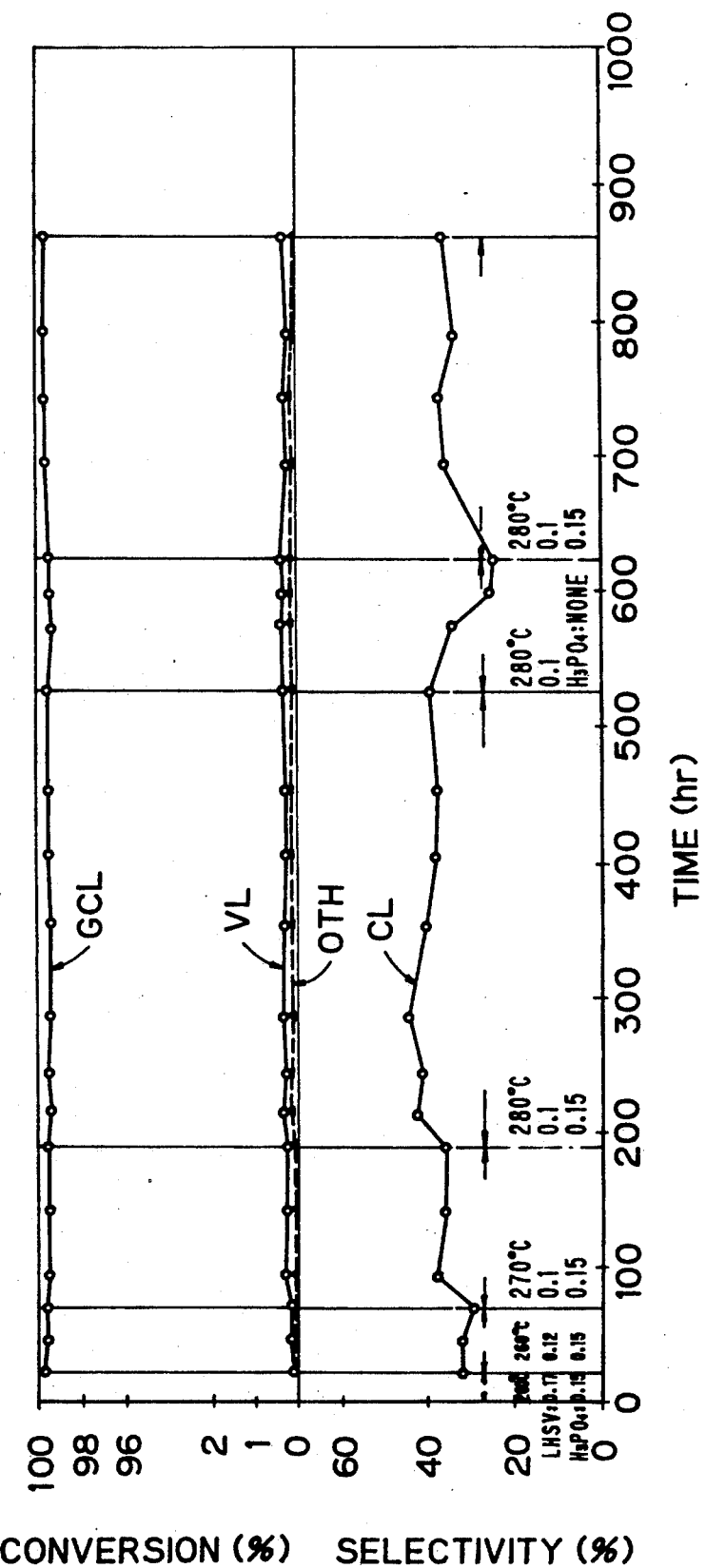
FIG. 2 is a graph showing changes in the conversion of catechol (CL) and the selectivities of guaiacol (GCL), veratrol (VL), and other by-products (OTH) with a lapse of the reaction time, when a catechol-methyl alcohol solution containing a catalytic amount of an active catalyst component (phosphoric acid) is fed into a reactor containing an inert sold carrier consisting of α-alumina grains with a pore volume of 0.3 ml/g and a specific surface area of 7.0 m$^2$/g, to cause the catechol to be mono-etherified with the methyl alcohol; and, FIG. 3 is a graph showing changes in the conversion of catechol (CL), and the selectivities of guaiacol (GLL), veratrol (VL) and other by-products (OTH) with a lapse of the reaction time, when a catechol-methyl alcohol solution containing a catalytic amount of phosphoric acid is fed into a reactor containing an inert solid carrier consisting of α-alumina grains, with a pore volume of 0.4 ml/g and a specific surface area of 48.1 m$^2$/g, to cause the catechol to be mono-etherified with the methyl alcohol.

These results are shown in Table 28 and FIG. 2.

TABLE 28

| Reaction time (hr) from start of reaction | Conversion of CL (%) | Selectivity (%) | | |
|---|---|---|---|---|
| | | GCL | VL | OTH |
| 21 | 31.73 | 99.77 | 0.11 | 0.12 |
| 45 | 31.76 | 99.70 | 0.19 | 0.11 |
| 69 | 29.56 | 99.75 | 0.19 | 0.06 |
| 93 | 38.20 | 99.56 | 0.33 | 0.11 |
| 141 | 36.14 | 99.64 | 0.27 | 0.09 |
| 189 | 36.14 | 99.63 | 0.27 | 0.10 |
| 213 | 42.39 | 99.53 | 0.33 | 0.14 |
| 243 | 41.10 | 99.57 | 0.29 | 0.14 |
| 285 | 44.34 | 99.49 | 0.36 | 0.15 |
| 357 | 40.25 | 99.51 | 0.33 | 0.16 |
| 405 | 38.14 | 99.58 | 0.29 | 0.13 |
| 453 | 37.71 | 99.57 | 0.29 | 0.14 |
| 525 | 39.48 | 99.56 | 0.31 | 0.13 |
| 573 | 33.97 | 99.43 | 0.40 | 0.16 |
| 597 | 25.69 | 99.54 | 0.32 | 0.14 |
| 621 | 24.25 | 99.51 | 0.34 | 0.14 |
| 693 | 35.76 | 99.70 | 0.18 | 0.12 |
| 741 | 36.60 | 99.61 | 0.24 | 0.15 |
| 789 | 32.51 | 99.75 | 0.21 | 0.04 |
| 861 | 35.95 | 99.67 | 0.30 | 0.03 |

EXAMPLE 18

The same procedures as those described in Example 17 were carried out, with the following exceptions.

The refractory glass reaction tube was replaced by a stainless steel reaction tube having an inside diameter of 30.7 mm and a length of 542 mm; the inert solid carrier consisted of 37.5 ml (31.97 g) of α-alumina grains having an average size of 3 mm, a pore volume of 0.4 ml/g, and a specific surface area of 48.1 m$^2$/g; and the feed gas G as mentioned in Example 17 was fed under the conditions as indicated in Table 29.

TABLE 29

| Reaction stage from start of reaction (hour) | Feed rate | | Temperature of center portion of inert solid carrier stratum (°C.) |
|---|---|---|---|
| | (g/hr) | LHSV (g/ml · hr) | |
| 0 to 264 | 7.5 | 0.10 | 270 |
| 265 to 577 | 7.5 | 0.10 | 260 |

The resultant reaction mixture gas was cooled to a temperature of 20° C. to collect a reaction product liquid comprising guaiacol, and the resultant reaction product liquids collected at the stages as indicated in Table 30 were subjected to the same gas chromatographic analysis as in Example 1.

Then, the conversion of catechol (CL), the selectivity of guaiacol (GCL), the selectivity of veratrol (VL) and the selectivity of other by-products (OTH), for example, methylated cyclic compounds) were calculated from the results of the analysis.

Figure 3:
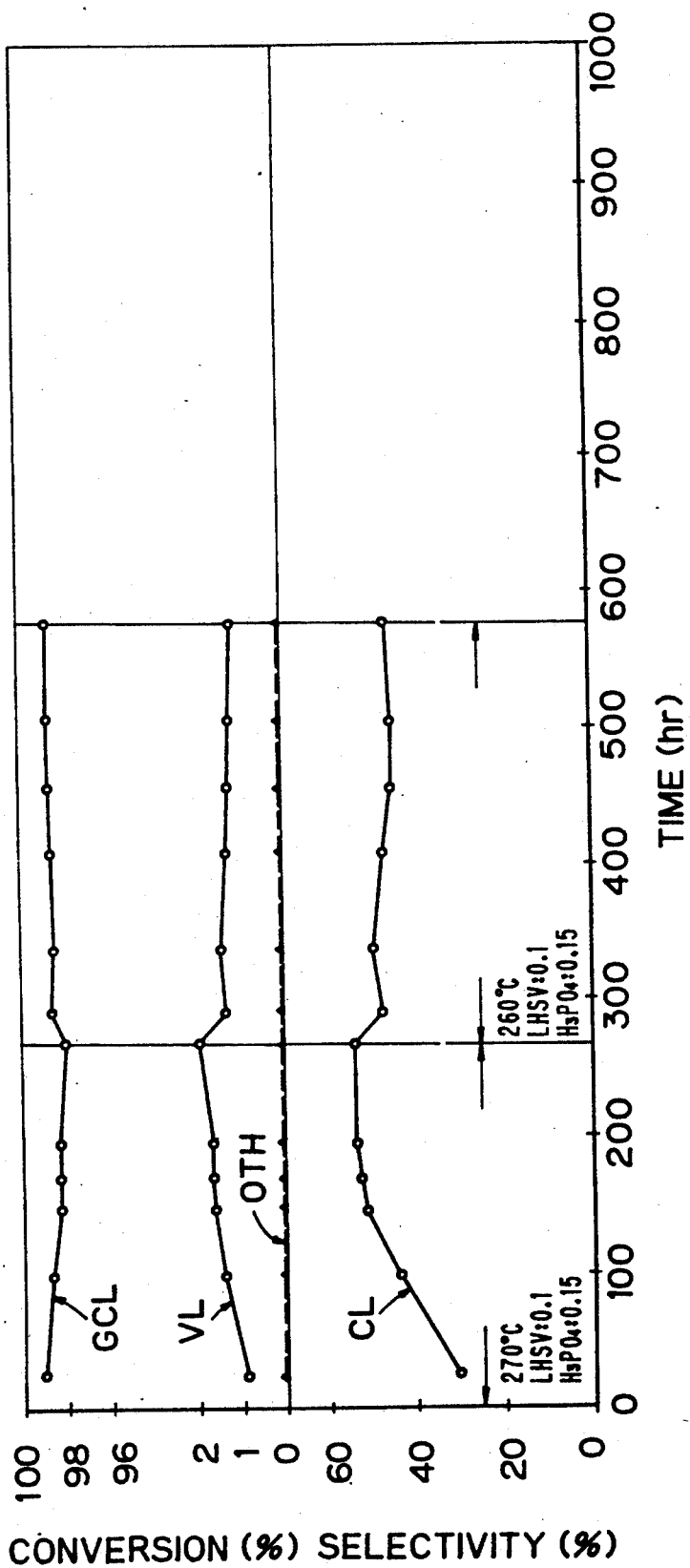

These results are shown in Table 30 and FIG. 3.

TABLE 30

| Reaction time (hr) from start of reaction | Conversion of CL (%) | Selectivity (%) | | |
|---|---|---|---|---|
| | | GCL | VL | OTH |
| 25 | 30.72 | 99.06 | 0.90 | 0.04 |
| 97 | 44.10 | 98.57 | 1.40 | 0.03 |
| 145 | 51.67 | 98.34 | 1.64 | 0.02 |
| 169 | 52.99 | 98.26 | 1.71 | 0.03 |
| 193 | 53.43 | 98.28 | 1.70 | 0.02 |
| 265 | 54.24 | 97.99 | 1.99 | 0.02 |
| 289 | 47.38 | 98.63 | 1.36 | 0.01 |
| 313 | 47.12 | 98.61 | 1.38 | 0.01 |
| 337 | 49.08 | 98.55 | 1.44 | 0.01 |

TABLE 30-continued

| Reaction time (hr) from start of reaction | Conversion of CL (%) | Selectivity (%) | | |
|---|---|---|---|---|
| | | GCL | VL | OTH |
| 409 | 47.64 | 98.62 | 1.32 | 0.06 |
| 457 | 45.60 | 98.64 | 1.26 | 0.08 |
| 505 | 45.58 | 98.68 | 1.25 | 0.07 |
| 577 | 46.26 | 98.73 | 1.20 | 0.07 |

EXAMPLE 19

The same refractory glass reaction tube as mentioned in Example 1 was charged with 25 ml (20.49 g) of an inert solid carrier consisting of α-alumina grains having an average size of 3 mm, a pore volume of 0.4 ml/g and a specific surface area of 48.1 m²/g, and then 90 ml of glass beads for preheating and having an diameter of 3 to 5 mm were placed at a bulk specific gravity of 1.52 on the α-alumina grain stratum.

The reaction tube was placed in an electric furnace having an inside diameter of 40 mm and a length of 300 mm, the temperature of the center portion of the inert solid carrier stratum was maintained at a level of 287° C., while flowing nitrogen gas at a flow rate of 20 ml/min through the reaction tube, and a feed gas derived from a solution of 50 parts by weight of catechol, 0.36 part by weight of an 85% phosphoric acid and 0.19 part by weight of orthoboric acid in 50 parts by weight of ethyl alcohol was fed into the reaction tube at a feed rate of 5.55 g/hr (LHSV: 0.11 g/ml.hr).

The resultant reaction mixture gas was cooled to a temperature of 20° C. to collect a reaction product liquid comprising catechol ethyl ether, and the resultant reaction product liquids collected at 40 hours after the start of the reaction were subjected to the same gas chromatographic analysis as in Example 1.

The results are shown in Table 31.

TABLE 31

| Reaction time (hr) from start of reaction | Conversion of CL (%) | Selectivity (%) | | |
|---|---|---|---|---|
| | | Catechol etylether | Catechol dietylether | OTH |
| 40 | 31.1 | 91.1 | 2.1 | 6.7 |

EXAMPLE 20

The same refractory glass reaction tube as mentioned in Example 1 was charged with 25 ml (20.49 g) of an inert solid carrier consisting of α-alumina grains having an average size of 3 mm, a pore volume of 0.4 ml/g and a specific surface area of 48.1 m²/g, and then 90 ml of glass beads for preheating and having an diameter of 3 to 5 mm were placed at a bulk specific gravity of 1.52 on the α-alumina grain stratum.

The reaction tube was placed in an electric furnace having an inside diameter of 40 mm and a length of 300 mm, the temperature of the center portion of the inert solid carrier stratum was maintained at 280° C., while flowing nitrogen gas at a flow rate of 20 ml/min through the reaction tube, and a feed gas derived from a solution of 25 parts by weight of hydroquinone and 0.5 parts by weight of an 85% phosphoric acid in 75 parts by weight of methyl alcohol, was fed at a feed rate of 30 g/hr (LHSV: 0.30 g/ml.hr) into the reaction tube.

The resultant reaction mixture gas was cooled to a temperature of 20° C. to collect a reaction product liquid comprising hydroquinone monomethylether, and the resultant reaction product liquid collected at 35 hours after the start of the reaction was subjected to the same gas chromatographic analysis as in Example 1.

The results are shown in Table 32.

TABLE 32

| Reaction time (hr) from start of reaction | Conversion of CL (%) | Selectivity (%) | | |
|---|---|---|---|---|
| | | Hydroquinone monomethyl ether | Hydroquinone dimethyl ether | OTH |
| 35 | 35.3 | 89.5 | 8.2 | 2.3 |

We claim:

1. A process for producing a monoalkylether of a dihydric phenol compound, comprising the steps of:
   (i) placing an inert solid carrier for a catalyst within a reactor, the inert solid carrier comprising at least one γ-alumina, activated carbon, titania, silica-alumina, member selected from the group consisting of α-alumina, θ-alumina-containing α-alumina, zeolite, kaolin, bentonite and acid clay;
   (ii) introducing a feed gas comprising a mixture of a dihydric phenol compound with a lower monohydric alcohol in a molar ratio of 1:1 to 1:50 into the reactor at a temperature of 200° C. to 400° C.;
   (iii) simultaneously introducing into the reactor an active component for the catalyst, comprising at least one member selected from the group consisting of:
     (a) phosphorus compounds which are orthophosphoric acid, alkyl phosphate, pyrophosphoric acid, metaphosphoric acid, tetraphosphoric acid, polymetaphosphoric acid and unhydrated phosphoric acid; and
     (b) mixtures of at least one of the above-mentioned phosphorus compounds (a) with at least one boron compound selected from the group consisting of orthoboric acid, alkyl borates, metaboric acid, tetraboric acid and boron oxide,
   in the above-mentioned mixtures (b), the atomic ratios of phosphorus to boron being from 1:0 to 1:10, whereby the introduced active component is impregnated in the inert solid carrier to provide a catalyst, and the introduced feed gas is brought into contact with the resultant catalyst; and
   (iv) collecting the resultant reaction product from said reaction mixture.

2. The process as claimed in claim 1, wherein the inert solid carrier is previously impregnated with the active catalyst component.

3. The process as claimed in claim 1, wherein the inert solid carrier is in the form of a number of solid grains.

4. The process claimed in claim 1, wherein the feed gas is intermittently mixed with an additional amount of the active catalyst component, to maintain the amount of the active catalyst component impregnated in the inert solid carrier and to control the amount of the active catalyst component impregnated in the inert solid carrier.

5. The process as claimed in claim 4, wherein the inert solid carrier grains have an average size of 1 to 10 mm.

6. The process as claimed in claim 1, wherein the inert solid carrier has a pore volume of 0.1 ml/g or more and a specific surface area (BET surface area) of 1 m²/g or more.

7. The process as claimed in claim 1, wherein the reaction product of the phosphorus compound and the boron compound comprises boron phosphate.

8. The process as claimed in claim 1 wherein, in the active catalyst component, the atomic ratio of phosphorus to boron is from 1:0 to 1:10.

9. The process as claimed in claim 1, wherein the dihydric phenol compound is selected from the group consisting of catechol, hydroquinone, resorcinol, 4-methyl catechol, 2-methyl catechol, 2-methyl hydroquinone, 4-chlorocatechol, 2-chlorocatechol and 2-chlorohydroquinone.

10. The process as claimed in claim 1, wherein the lower monohydric alcohol compound is selected from aliphatic monohydric alcohols having 1 to 6 carbon atoms.

11. The process as claimed in claim 1, wherein the amount of the dihydric phenol compound in the feed gas is from 0.01 to 1.0 g/hr per $cm^3$ of the inert solid carrier.

12. The process as claimed in claim 1 wherein, in the collecting step, the reaction gas mixture is cooled to a temperature of 40° C. or less.

* * * * *

UNITED STATES PATENT AND TRADEMARK OFFICE
CERTIFICATE OF CORRECTION

PATENT NO. : 5,189,225
DATED : February 23, 1993
INVENTOR(S) : Shinichi Furusaki et al.

It is certified that error appears in the above-indentified patent and that said Letters Patent is hereby corrected as shown below:

Claim 1, column 24, lines 19-22

"one $\gamma$-alumina, activated carbon, titania, silica-alumina, member selected from the group consisting of $\alpha$-alumina, $\theta$-alumina containing $\alpha$-alumina,"

should be

--one member selected from the group consisting of $\alpha$-alumina, $\theta$-alumina containing $\alpha$-alumina, $\gamma$-alumina, activated carbon, titania, silica-alumina,-- and

Claim 5, col. 24, line 62, "claim 4" should be --claim 3--.

Signed and Sealed this

Fourteenth Day of December, 1993

Attest:

BRUCE LEHMAN

*Attesting Officer*    *Commissioner of Patents and Trademarks*